United States Patent
Reichert et al.

(10) Patent No.: US 7,923,540 B2
(45) Date of Patent: Apr. 12, 2011

(54) 2-[[1-[[(2,3-DIHYDRO-2-OXO-1H-BENZI-MIDAZOL-5-YL)AMINO]CARBONYL]-2-OXOPROPYL]AZO]-BENZOIC ACID AND A PROCESS FOR ITS PREPARATION

(75) Inventors: Hans Reichert, Rheinfelden (DE); Max Hügin, Rünenberg (CH); Ulrich Veith, Hockessin, DE (US); Sibylle Soder, Möhlin (CH); Thomas Eichenberger, Basel (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/087,834

(22) PCT Filed: Jan. 8, 2007

(86) PCT No.: PCT/EP2007/050148
§ 371 (c)(1),
(2), (4) Date: Jul. 16, 2008

(87) PCT Pub. No.: WO2007/082813
PCT Pub. Date: Jul. 26, 2007

(65) Prior Publication Data
US 2009/0012305 A1  Jan. 8, 2009

(30) Foreign Application Priority Data
Jan. 18, 2006  (EP) .................... 06100541

(51) Int. Cl.
*C09B 29/32* (2006.01)
*C09B 29/03* (2006.01)
*C09B 41/00* (2006.01)
*C09B 67/48* (2006.01)

(52) U.S. Cl. ........ 534/575; 534/705; 534/887; 106/496; 524/93

(58) Field of Classification Search .................. None
See application file for complete search history.

(56) References Cited

U.S. PATENT DOCUMENTS

| 4,024,124 A | 5/1977 | Ribka ............................ 260/157 |
| 4,906,735 A | 3/1990 | Hunger ........................ 534/575 |
| 6,835,242 B2 * | 12/2004 | Nickel et al. ................. 106/493 |

FOREIGN PATENT DOCUMENTS

JP  08-269347  * 10/1996

OTHER PUBLICATIONS

Machine Translation of JP 08-269347, Oct. 15, 1996.*

* cited by examiner

*Primary Examiner* — Fiona T Powers
(74) *Attorney, Agent, or Firm* — Shiela A. Loggins; Qi Zhuo

(57) ABSTRACT

The present invention is directed to 2-[[1-[[(2,3-dihydro-2-oxo-1H-benzimidazol-5-yl)amino]carbonyl]-2-oxo-propyl]azo]-benzoic acid (C.I. Pigment Yellow 151): (I), characterized by a $\Delta E^*$ (black/white) in masstone below 22.0±0.7, a process for its preparation and its use for pigmenting macromolecular organic materials of natural or synthetic origin. The pigment has high opacity and high color strength.

6 Claims, 2 Drawing Sheets

Transmission Electron Micrograph of Hostaperm® Yellow H4G (Clariant AG)

Transmission Electron Micrograph of C.I. Pigment Yellow 151 according to the Present Invention … # 2-[[1-[[(2,3-DIHYDRO-2-OXO-1H-BENZIMIDAZOL-5-YL)AMINO]CARBONYL]-2-OXOPROPYL]AZO]-BENZOIC ACID AND A PROCESS FOR ITS PREPARATION The present invention is directed to 2-[[1-[[(2,3-dihydro-2-oxo-1H-benzimidazol-5-yl)amino]carbonyl]-2-oxopropyl]azo]-benzoic acid (C.I. Pigment Yellow 151)

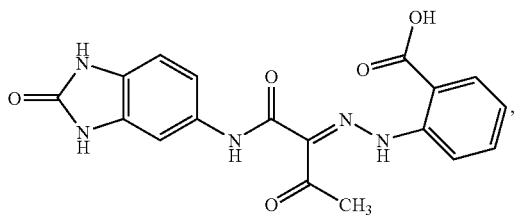

characterized by a ΔE* (black/white) in masstone below 22.0±0.7, a process for its preparation and its use for pigmenting macromolecular organic materials of natural or synthetic origin. The pigment has high opacity and high color strength.

U.S. Pat. No. 4,024,124 describes monoazo acetoacetylaminobenzimidazolone pigments containing carboxy group. In example 1 the preparation of C.I. Pigment Yellow 151 is disclosed. The crude pigment obtained by coupling in an aqueous medium is dried after isolation, powdered, refluxed for 2 hours in glacial acetic acid, suction-filtered, washed and dried. A pigment of soft grain, good tinctorial strength and clear shade is obtained in this manner.

U.S. Pat. No. 4,906,735 discloses an improved process for the manufacture of C.I. Pigment Yellow 151 by coupling the components in an aqueous medium in the presence of an oxethylation product of an alcohol or alcohol mixture having from 8 to 14 carbon atoms and 3 to 10 mols of ethylene oxide, and heating the aqueous pigment suspension after complete coupling. The pigment thus obtained avoids an after-treatment in anhydrous organic solvents. The pigment is obtained in a form, which can be compared with that of example 1 of U.S. Pat. No. 4,042,124.

It is the object of the present invention to provide a novel 2-[[1-[[(2,3-dihydro-2-oxo-1H-benzimidazol-5-yl)amino]carbonyl]-2-oxopropyl]azo]-benzoic acid (C.I. Pigment Yellow 151) having unique and surprising color characteristics.

Accordingly, the present invention relates to 2-[[1-[[(2,3-dihydro-2-oxo-1H-benzimidazol-5-yl)amino]carbonyl]-2-oxopropyl]azo]-benzoic acid (C.I. Pigment Yellow 151):

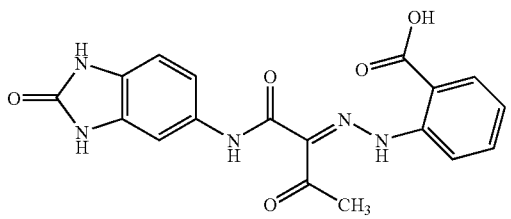

having a ΔE* (black/white) in masstone below 22.0±0.7, especially below 20±0.7, very especially below 19±0.7.

The color strength of the compound (pigment) is 6 to 55%, especially 10 to 36% higher than the color strength of C.I. Pigment Yellow 151 HOSTAPERM Yellow H4G (Clariant AG) as standard in white reduction (5:95).

The 2-[[1-[[(2,3-dihydro-2-oxo-1H-benzimidazol-5-yl)amino]carbonyl]-2-oxopropyl]azo]-benzoic acid having an essentially cubic to cuboidal particle shape with an average particle size ($D_{50}$%) in the range of 0.30 to 0.45 µm, especially below 0.40, very especially in the range of 0.34 to 0.39 measured by Joyce Löbl disc centrifuge and a specific surface area (BET) in the range of 20 to 25 $m^2/g$ shows high opacity and high color strength and excellent weatherability behavior. As shown by electron microscopy, the average aspect ratio of length to width and/or height is below 1:2.5 with respect to the majority of the particles.

Figure 1:
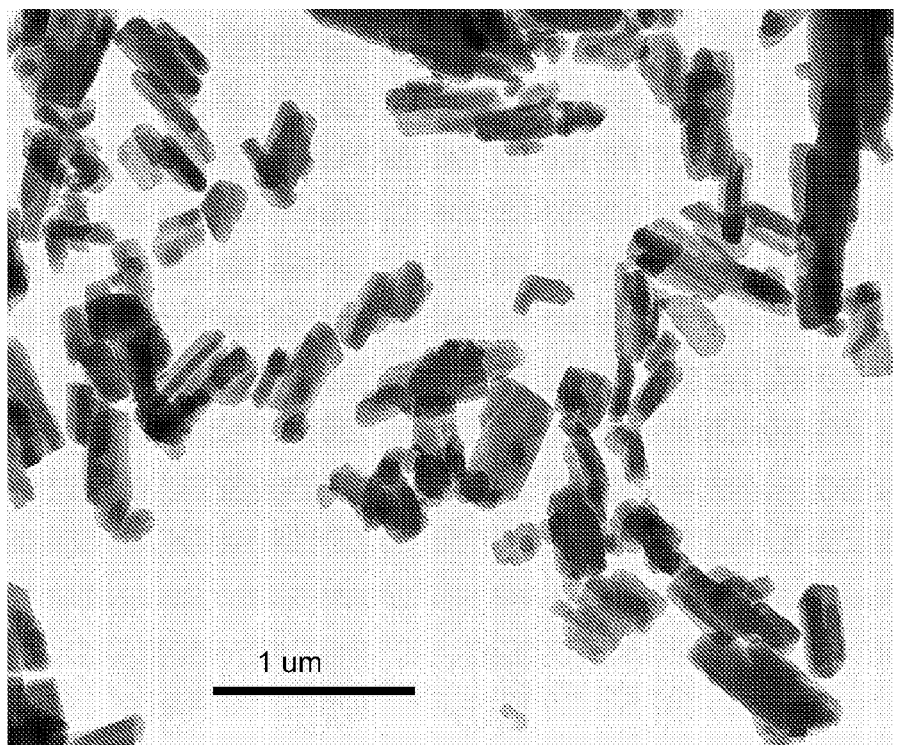
FIG. 1 is a transmission electron micrograph (TEM) of HOSTAPERM Yellow H4G (Clariant AG; 2-[[1-[[(2,3-dihydro-2-oxo-1H-benzimidazol-5-yl)amino]carbonyl]-2-oxopropyl]azo]-benzoic acid; C.I. Pigment Yellow 151).
Figure 2:
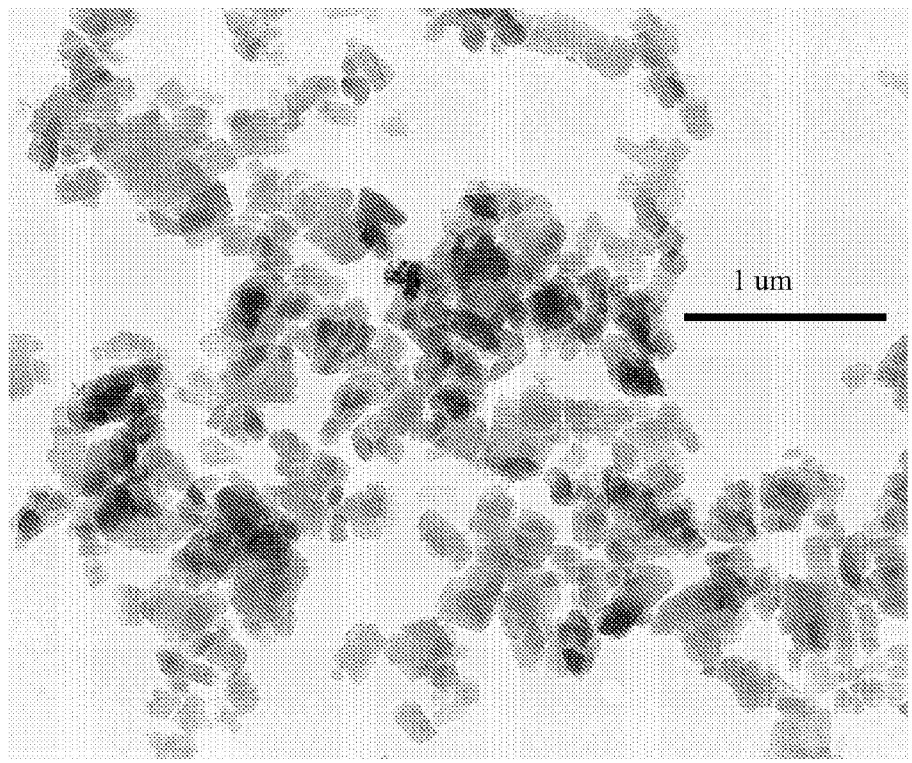
FIG. 2 is a TEM of 2-[[1-[[(2,3-dihydro-2-oxo-1H-benzimidazol-5-yl)amino]carbonyl]-2-oxopropyl]azo]-benzoic acid (C.I. Pigment Yellow 151) according to the present invention.

As evident from the TEMs the pigment of the present invention has a cubic, or cuboidal particle form, whereas C.I. Pigment Yellow 151 HOSTAPERM Yellow H4G has a more rod-like particle form.

The C.I.E. color space values of the pigment of the present invention in masstone measured as described in Application Example 1b are
L*=83.9-85.6, especially 84.3-85.6,
C*=86.1-90.1, especially 86.3-90.1,
h=86.4-88.4, especially 86.6-88.4.

The C.I.E. color space values of the pigment of the present invention in white reduction (5:95) measured as described in Application Example 1c are
L*=92.6-93.4,
C*=42.7-50.9,
h=96.9-98.3.

In addition, the invention provides a process for the manufacture of the compound of the formula

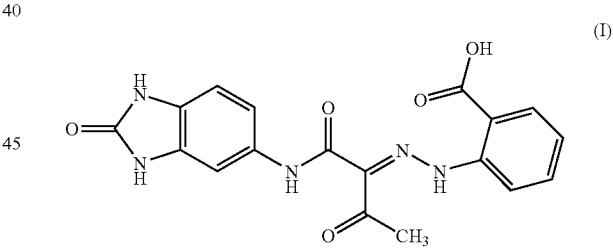

by coupling of diazotized anthranilic acid (1-aminobenzene-2-carboxylic acid) with 5-acetoacetylamino-benzimidazolone in an aqueous medium followed by a thermal after-treatment, wherein the thermal after-treatment is carried out at a pH above 5.5.

The thermal after-treatment is especially carried out at a pH of from 6.0-7.3, very especially 6.5-7.3.

Advantageously, the preferably aqueous solutions or suspensions of the starting materials are fed to the reactor continuously, subsequently, or simultaneously and preferably in equivalent amounts. The classic process assistants such as resins, surfactants and other additives may likewise be used in the process of the invention.

The starting material for the diazotization reaction is anthranilic acid (1-aminobenzene-2-carboxylic acid).

The coupling component is 5-acetoacetylamino-benzimidazolone.

The azo coupling is preferably carried out in aqueous solution, but it is also possible to use organic solvents, if appropriate mixed with water, for example aromatic hydrocarbons, hydrochlorocarbons, glycol ethers, nitriles, esters, dimethylformamide, tetramethylurea and N-methylpyrrolidone.

Diazotizations are carried out at temperatures of −15 to +80° C., preferably −12 to +10° C., and azo couplings at −10 to 90° C., preferably at −5 to 40° C.

The diazotisation is carried out, for example, with a nitrite, for example an alkali metal nitrite, such as sodium nitrite, in a medium containing a mineral acid, for example in a medium containing hydrochloric acid, generally at temperatures of from −15 to 80° C., preferably from −12 to 10° C. Excess nitrite is destroyed with standard scavengers such as urea or sulfamic acid.

The coupling to the coupling component is effected in a manner known per se, at acidic or neutral to weakly alkaline pH values, for example a pH value of from 1 to 8, and tempera-tures of, for example, from −10 to 90° C., preferably from −5 to 40° C.

To carry out the azo coupling reaction according to the invention, a solution or suspension of the diazonium salt and a solution or suspension of the coupling component can be continuously, subsequently, or simultaneously introduced into a reactor and continuously mixed with each other therein and reacted.

The process according to the invention is advantageously carried out by slowly adding a solution or suspension of the coupling component, especially a basic solution or suspension of the coupling component to a freshly prepared solution or suspension of the diazotised compound. After the reaction is almost completed, the pH is maintained in the neutral range, for example at from pH 4.5 to 8, especially 4.5 to 7.0, very especially 6.1 to 7.0 by addition of an aqueous alkali metal hydroxide solution, such as sodium hydroxide solution. The resulting pigment suspension is stirred until the reaction is complete followed by the thermal aftertreatment. The product is isolated by filtration. The obtained presscake is dried in an oven with or without vacuum and finally pulverized or pulverized and sieved.

For both the diazotization and the azo coupling, the reactant solutions may be admixed with buffer solutions, preferably of organic acids and salts thereof, for example acetic acid/acetate buffer, citric acid/citrate buffer, or of inorganic acids and salts thereof, for example phosphoric acid/phosphate or carbonic acid/carbonate.

Advantageously, sodium dihydrogenphosphate, or sodium acetate is added to the diazo solution before the coupling reaction.

After termination of the addition the pigment suspension is optionally diluted with water and heated for 1 to 24 hours, especially 6 to 15 hours at a temperature above 80° C., especially of from 90 to 110° C., very especially 98 to 102° C. at a pH above 5.5, especially 6.0-7.3, very especially 6.5-7.3. The pH is adjusted by addition of an acid, especially a weak acid, preferably acetic acid. Subsequently, the pigment is isolated from the suspension, washed, dried and optionally pulverized.

The pigment of the invention is useful for pigmenting macromolecular organic materials of natural or synthetic origin, for example plastics, resins, coatings, paints or electrophotographic toners and developers and also inks, including printing inks.

The pigment prepared according to the invention is useful for dyeing or printing hydroxyl-containing or nitrogenous natural organic and also synthetic substrates. Such substrates include for example synthetic or natural fiber materials and also leather materials comprising predominantly natural or regenerated cellulose or natural or synthetic polyamides. It is particularly useful for dyeing and printing textile material based on acetate, polyester, polyamide, polyacrylonitrile, PVC and polyurethane fibers and also wool or in particular cotton. To this end, the pigment can be applied to the textile materials by the usual exhaust, padding or printing processes.

The pigment of the invention is useful as colorant in electrophotographic toners and developers, for example one- or two-component powder toners (also known as one- or two-component developers), magnet toners, liquid toners, latex toners, polymerization toners and also specialty toners.

Typical toner binders are addition polymerization, polyaddition and polycondensation resins, such as styrene, styrene-acrylate, styrene-butadiene, acrylate, polyester, phenol-epoxide resins, polysulfones, polyurethanes, individually or in combination, and also polyethylene and polypropylene, which may each include further ingredients, such as charge control agents, waxes or flow assistants, or are subsequently modified with these additives.

The pigment of the invention is further useful as colorant in powders and powder coatings, especially in triboelectrically or electrokinetically sprayable powder coatings used for surface coating of objects composed for example of metal, wood, plastic, glass, ceramic, concrete, textile material, paper or rubber.

Powder coating resins used are typically epoxy resins, carboxyl- and hydroxyl-containing polyester resins, polyurethane and acrylic resins together with customary hardeners. Combinations of resins are also used. For instance, epoxy resins are frequently used in combination with carboxyl- and hydroxyl-containing polyester resins. Typical hardener components (depending on the resin system) include for example acid anhydride, imidazoles and also dicyandiamide and derivatives thereof, capped isocyanates, bisacylurethanes, phenolic and melamine resins, triglycidyl isocyanurates, oxazolines and dicarboxylic acids. The pigment of the invention is also useful as colorant in inks, preferably inkjet inks, for example on an aqueous or nonaqueous basis, microemulsion inks and also in such inks as operate according to the hot-melt principle.

Inkjet inks generally include a total of 0.5 to 15% by weight, preferably 1.5 to 8% by weight, (reckoned dry) of one or more of the compounds according to the invention. Microemulsion inks are based on organic solvents and water with or without an additional hydrotropic substance (interface mediator). Microemulsion inks include 0.5 to 15% by weight, preferably 1.5 to 8% by weight, of one or more of the compounds according to the invention, 5 to 99% by weight of water and 0.5 to 94.5% by weight of organic solvent and/or hydrotropic compound.

Solvent based inkjet inks preferably include 0.5 to 15% by weight of one or more compounds according to the invention, 85 to 99.5% by weight of organic solvent and/or hydrotropic compounds.

Hot-melt inks are based mostly on waxes, fatty acids, fatty alcohols or sulfonamides that are solid at room temperature and liquefy on heating, the preferred melting range lying between about 60° C. and about 140° C. Hot-melt inkjet inks consist essentially for example of 20 to 90% by weight of wax and 1 to 10% by weight of one or more of the compounds according to the invention. They may further include 0 to 20% by weight of an additional polymer (as "dye solvent"), 0 to 5% by weight of dispersant, 0 to 20% by weight of viscosity modifier, 0 to 20% by weight of plasticizer, 0 to 10% by weight of tack additive, 0 to 10% by weight of transparency stabilizer (prevents crystallization of waxes, for example) and also 0 to 2% by weight of antioxidant. Typical additives and assistants are described for example in U.S. Pat. No. 5,560,760.

The pigment of the invention is also useful as colorant for color filters and also for additive as well as subtractive color generation.

The Examples that follow illustrate the invention without limiting the scope thereof. Unless otherwise indicated, percentages and parts are percentages and parts by weight, respectively.

EXAMPLES

Example 1

29.15 g 2-Aminobenzoic acid are added to a mixture of 200 g water and 98.05 g hydrochloric acid (32% strength). The suspension is cooled to 0° C. and treated with 61.2 g sodium nitrite solution (ca. 24% strength) during 30 minutes keeping the temperature at 0° C. The clear solution is stirred for 30 minutes and diluted with 140 g ice and water. Excess of nitrite is destroyed with sulfamic acid solution (20% strength). To the clear solution are added 76 g water and 21.12 g disodiumhydrogenphosphate, which was dissolved in 106 g water. The solution is cooled with 91 g ice and water and treated with 45.3 g sodium hydroxide solution (30%) and 202 g ice and water.

Half of the diazo solution (580 g) is treated with a solution of 25 g 5-acetoacetylamino-benzimidazolone in 42 g water and 25 g sodium hydroxide solution (30%) at 0° C. during 1 hour. 10 minutes after the coupling solution has been added, pH 6.3 is monitored. The orange yellow pigment suspension is heated to 20° C., treated with additional 260 g water and heated to 99-100° C. for 15 hours (pH 7.1-7.2). The pH is adjusted with 10.3 g acetic acid (50%) to pH 5.9 and the suspension is stirred for another 3 hours at 99-100° C. The suspension is cooled to 70° C., filtered and washed with water. The presscake is dried in an oven and finally pulverized (yield: 36.5 g).

| | | | Masstone | | | | |
|---|---|---|---|---|---|---|---|
| Pigment | L* | C* | h | ΔC* | ΔH* | ΔE* (b/w) | ΔTr |
| HOSTAPERM Yellow H4G, C.I. Pigment Yellow 151 | 85.2 | 89.6 | 87.2 | Standard | Standard | 23.2 | Standard |
| Sample from example 1 | 85.8 | 89.3 | 87.0 | −0.4 | 0.3 R | 19.2 | −3.5 |

| | White Reduction | | | |
|---|---|---|---|---|
| Pigment | L* | C* | h | Color Strength |
| HOSTAPERM Yellow H4G, C.I. Pigment Yellow 151 | 93.6 | 43.4 | 97.7 | Standard |
| Sample from example 1 | 93.4 | 44.4 | 96.9 | +9% |

Example 2

29.15 g 2-Aminobenzoic acid are added to a mixture of 200 g water and 98.05 g hydrochloric acid (32% strength). The suspension is cooled to 0° C. and treated with 61.2 g sodium nitrite solution (ca. 24% strength) during 30 minutes keeping the temperature at 0° C. The clear solution is stirred for 30 minutes and diluted with 140 g ice and water. Excess of nitrite is destroyed with sulfamic acid solution (20% strength). To the clear solution are added 76 g water and 28.94 g sodium acetate trihydrate, which was dissolved in 60 g water. The solution is cooled with 40 g water and 91 g ice and treated with 45.3 g sodium hydroxide solution (30%) and 202 g ice and water. Half of the diazo solution (585 g) is treated with a solution of 25 g 5-acetoacetylamino-benzimidazolone in 42 g water and 25 g sodium hydroxide solution (30%) at 0° C. during 1 hour. 5 minutes after the coupling solution has been added a pH 5.8 is monitored. The orange yellow pigment suspension is heated to 20° C., treated with additional 260 g water and heated to 99-100° C. for 15 hours (pH 7.2-7.3). The pH is adjusted with 6.5 g acetic acid (50%) to pH 5.8 and stirred for another 3 hours at 99-100° C. The suspension is cooled to 70° C., filtered and washed with water. The presscake is dried in an oven with vacuum and finally pulverized and sieved. The yield obtained was 34.5 g.

| | | | Masstone | | | | |
|---|---|---|---|---|---|---|---|
| Pigment | L* | C* | h | ΔC* | ΔH* | ΔE* (b/w) | ΔTr |
| HOSTAPERM Yellow H4G, C.I. Pigment Yellow 151 | 85.2 | 89.6 | 87.2 | Standard | Standard | 23.2 | Standard |
| Sample from example 2 | 85.1 | 88.0 | 87.5 | −1.6 | 0.5 G | 18.9 | −3.3 |

| | White Reduction | | | |
|---|---|---|---|---|
| Pigment | L* | C* | h | Color Strength |
| HOSTAPERM Yellow H4G, C.I. Pigment Yellow 151 | 93.6 | 43.4 | 97.7 | Standard |
| Sample from example 2 | 93.4 | 46.8 | 97.3 | +27% |

Example 3

29.15 g 2-Aminobenzoic acid are added to a mixture of 200 g ice-water and 98.0 g hydrochloric acid (32% strength). The suspension is cooled to 1° C. and treated with 52.4 ml g sodium nitrite solution (ca. 28% strength) during 20 minutes keeping the temperature at 0-1° C. The clear solution is stirred for 30 minutes and treated with additional 2 ml of sodium nitrite solution. The clear solution is diluted with 143 g water keeping the temperature at 0° C. Excess of nitrite is destroyed with sulfamic acid solution (20% strength). To the clear solution are added 75 g water and 87.07 g disodiumhydrogenphosphate aqueous solution (25% strength). The solution is cooled with 215 g ice and water and treated with 45.3 g sodium hydroxide solution (30%) and 202 g ice and water. The diazo solution is treated with a solution of 50 g 5-acetoacetylamino-benzimidazolone in 150 g water and 54.6 g sodium hydroxide solution (30%) at 0-7° C. during 1 hour. 10 minutes after the coupling solution has been added a pH 6.6 is monitored. Half of the orange yellow pigment suspension is heated to 20° C., treated with additional 500 g water and heated to 95° C. for 15 hours (pH 7.1-7.3). The pH is adjusted with 13 g acetic acid (50%) to pH 6.0 and stirred for another 3 hours at 95° C. The suspension is cooled to 70° C., filtered and washed with water. The presscake is dried in an oven and finally pulverized. The yield obtained is 33.9 g.

| | | | Masstone | | | | |
|---|---|---|---|---|---|---|---|
| Pigment | L* | C* | h | ΔC* | ΔH* | ΔE* (b/w) | ΔTr |
| HOSTAPERM Yellow H4G, C.I. Pigment Yellow 151 | 85.1 | 89.7 | 87.3 | Standard | Standard | 23.2 | Standard |
| Sample from example 3 | 84.4 | 88.3 | 87.1 | −1.4 | 0.3 R | 20.6 | −1.4 |

| | White Reduction | | | |
|---|---|---|---|---|
| Pigment | L* | C* | h | Color Strength |
| HOSTAPERM Yellow H4G, C.I. Pigment Yellow 151 | 93.5 | 44.0 | 97.1 | Standard |
| Sample from example 3 | 93.2 | 47.1 | 96.7 | +25% |

Comparative Example 1

Example 1 of U.S. Pat. No. 4,906,735

13.7 g of anthranilic acid are stirred with 250 ml of water and 50 ml of 5N hydrochloric acid, and diazotized with 20 ml of 5N sodium nitrite solution. This diazo solution is poured at 25° C. with stirring into an acetic suspension of the coupling component, which is prepared as follows: 24 g of 5-acetoacetylamino-benzimidazolone are stirred at room temperature with 200 ml of water, and dissolved by adding 60 ml of 5N sodium hydroxide solution. The solution was clarified by means of active charcoal, and the filtrate is added dropwise within 30 minutes while stirring to a solution of 30 ml of water, 41 ml of glacial acetic acid, 80 ml of 5N sodium hydroxide solution and 3 g of LUTEWSOL OW 50 (BASF AG).

The coupling being complete (pH ~5.1), the suspension is heated to 95-97° C. by introducing steam, and maintained for 3 hours at this temperature. At 60-70° C., the suspension is filtered, the press cake is washed free from salt, dried and ground.

| | | | Masstone | | | | |
|---|---|---|---|---|---|---|---|
| Pigment | L* | C* | h | ΔC* | ΔH* | ΔE* (b/w) | ΔTr |
| HOSTAPERM Yellow H4G, C.I. Pigment Yellow 151 | 84.7 | 89.1 | 87.4 | Standard | Standard | 22.8 | Standard |
| Sample from Comparative Example 1 | 83.2 | 88.3 | 87.1 | −0.8 | 0.4 R | 50.4 | +27.5 |

| | White Reduction | | | |
|---|---|---|---|---|
| Pigment | L* | C* | h | Color Strength |
| HOSTAPERM Yellow H4G, C.I. Pigment Yellow 151 | 93.2 | 43.1 | 97.9 | Standard |
| Sample from Comparative Example 1 | 93.5 | 44.3 | 100.4 | +4% |

Application Example 1

Determination of Color a) Millbase Formulation

A 250 ml jar is charged with 100 grams of 2 mm diameter glass beads is charged with 2.50 g pigment obtained above, 0.85 g DISPERBYK 161 and 46.65 clear finish (Anreibelack AM90) (1). The mixture in the jar is shaken on a Skandex shaker (Skandex Disperser BA S20) for 2 hours (DIN 53238 Part 13). The millbase contains 5% pigment with a pigment/binder ratio of 1/9.

b) Masstone Color

The above millbase is applied onto a black-and-white-contrast chart by means of a 100 μm rakel coater (Spiralrakel). The coating is air-dried for 30 minutes and then baked at 130° C. for 30 minutes, yielding a yellow colored chart. The following color characteristic data are measured on the coated chart using a Minolta 3600d spectrophotometer equipped with the CGREC software: C.I.E. L*, C*, h color space value numbers using a D65 illuminant and 10° observer; ΔTr; ΔE* (black/white).

c) White Reduction (5:95 (Pigment:TiO$_2$)):

A 100 ml jar is charged with 23.75 white finish (2.2) and 6.25 g of the above millbase formulation. The formulation is homogenously blended for 5 minutes in a mixer (Farbmischer FAS 500) and applied onto a white chart by means of a 100 μm rakel coater (Spiralrakel). The coating is air-dried for 30 minutes and then baked at 130° C. for 30 minutes. The following color data are measured on the coated chart using a Minolta 3600d spectrophotometer equipped with the CGREC software: C.I.E. L*, C*, h color space value numbers using a D65 illuminant and 10° observer; color strength.

Clear Finish (1):

| | |
|---|---|
| Alkydal F310 (60% in solvent naphta) | 54.62 g |
| Xylene | 17.29 g |
| Butanol | 1.84 g |
| 1-Methoxy-2-propanol | 1.84 g |
| Silikon oil A (1% in Xylene) | 0.91 g |
| Maprenal MF 650 (55% in iso-butylacetate) | 23.50 g |

White Finish (2):

| Millbase formulation (2.1) | |
| --- | --- |
| TiO$_2$ | 55.00 g |
| Alkydal F310 | 34.36 g |
| EFKA 4401 | 1.76 g |
| Aerosil 200 | 0.50 g |
| Silicone oil A (1% in xylene) | 1.00 g |
| 1-Methoxy-2-Propanol | 1.10 g |
| Butanol | 1.10 g |
| Xylene | 5.18 g |

The above millbase is dispersed on a pearl mill.

| Let Down formulation (2.2) | |
| --- | --- |
| Millbase (2.1) | 45.45 g |
| Alkydal F310 | 33.65 g |
| Maprenal MF 650 | 17.90 g |
| TINUVIN 123, hindered amine light stabilizer | 0.60 g |
| Xylene | 2.40 g |

The above components are homogenously blended for 30 minutes on a stirrer.

The invention claimed is:

1. 2-[[1-[[(2,3-dihydro-2-oxo-1H-benzimidazol-5-yl)amino]carbonyl]-2-oxopropyl]azo]-benzoic acid

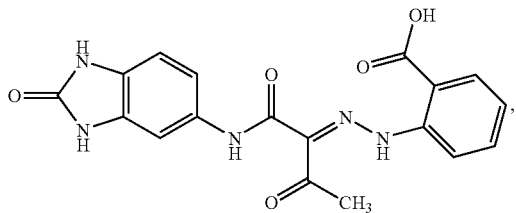

having a cubic, or a cuboidal particle form, and a ΔE* (black/white) in masstone below 22.0±0.7.

2. 2-[[1-[[(2,3-dihydro-2-oxo-1H-benzimidazol-5-yl)amino]carbonyl]-2-oxopropyl]azo]-benzoic acid

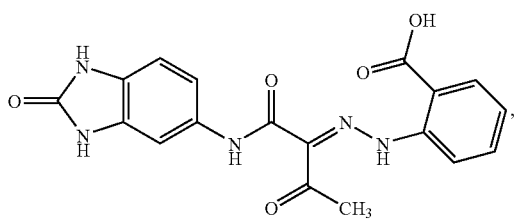

having a cubic, or a cuboidal particle form, and a ΔE* (black/white) in masstone below 22.0±0.7, wherein the color strength of the compound is 6 to 55%, higher than the color strength of C. I. Pigment Yellow 151 HOSTAPERM Yellow H4G (Clariant AG) as standard in white reduction (5:95).

3. A process for the manufacture of the compound of the formula

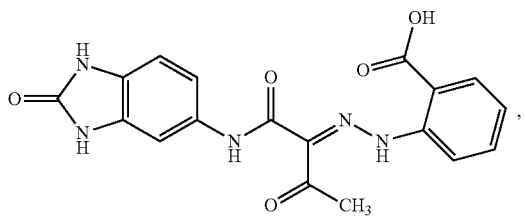

comprising coupling of diazotized anthranilic acid (1-aminobenzene-2-carboxylic acid) with 5-acetoacetylamino-benzimidazolone in an aqueous medium and a thermal after-treatment, wherein the thermal after-treatment is carried out at a pH of from 6.0-7.3 at a temperature of from 90 to 110° C.

4. A compound,

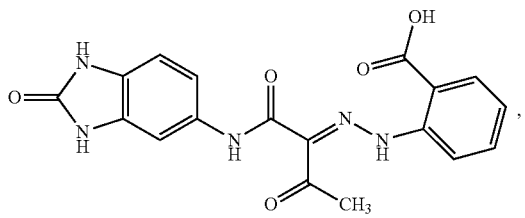

obtained by the process of claim 3.

5. Macromolecular organic materials of natural or synthetic origin pigmented with a compound of claim 1.

6. The 2-[[1-[[(2,3-dihydro-2-oxo-1H-benzimidazol-5-yl)amino]carbonyl]-2-oxopropyl]azo]benzoic acid

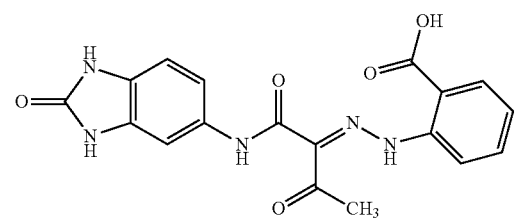

according to claim 1, having a ΔE* (black/white) in masstone below 20.0±0.7.

* * * * *